United States Patent
Wright et al.

(10) Patent No.: US 11,825,206 B2
(45) Date of Patent: Nov. 21, 2023

(54) MAPPING PULSE PROPAGATION

(71) Applicant: Nokia Technologies Oy, Espoo (FI)

(72) Inventors: Christopher Wright, London (GB); Harry Cronin, Cambridge (GB); Phil Catton, Cambridge (GB); William Schnabel, Surrey (GB)

(73) Assignee: Nokia Technologies Oy, Espoo (FI)

( * ) Notice: Subject to any disclaimer, the term of this patent is extended or adjusted under 35 U.S.C. 154(b) by 60 days.

(21) Appl. No.: 17/707,626

(22) Filed: Mar. 29, 2022

(65) Prior Publication Data
US 2022/0329718 A1  Oct. 13, 2022

(30) Foreign Application Priority Data
Apr. 12, 2021 (EP) .................................. 21167919

(51) Int. Cl.
*G06T 7/90* (2017.01)
*A61B 5/024* (2006.01)
(Continued)

(52) U.S. Cl.
CPC ............... *H04N 23/73* (2023.01); *G06T 7/90* (2017.01); *G06V 10/74* (2022.01); *H04N 23/45* (2023.01);
(Continued)

(58) Field of Classification Search
CPC ...... H04N 23/73; H04N 23/70; H04N 25/531; H04N 25/532; G03B 9/14; G03B 7/00;
(Continued)

(56) References Cited

U.S. PATENT DOCUMENTS

| 9,854,976 B2 * | 1/2018 | Takamori | ........... A61B 5/02125 |
| 10,004,410 B2 * | 6/2018 | Porges | ..................... A61B 5/08 |

(Continued)

FOREIGN PATENT DOCUMENTS

| CN | 111429345 A | 7/2020 |
| CN | 112006673 A | 12/2020 |

(Continued)

OTHER PUBLICATIONS

"A short selfie video on your smartphone can now measure your blood pressure", New Atlas, Retrieved on Mar. 31, 2022, Webpage available at : https://newatlas.com/smartphone-app-measure-blood-pressure-face-camera/61002/.

(Continued)

*Primary Examiner* — Brian P Yenke
(74) *Attorney, Agent, or Firm* — Nokia Technologies Oy

(57) ABSTRACT

Examples of the disclosure relate to at least apparatus, methods, and computer programs, configured to control capture of two images of an area, across which a pulse propagates, using different shutter scanning directions. Either the images are converted into pulse-phase maps of the area and a pulse-phase difference map obtained which identifies differences between the pulse-phase maps of the area, or a colour difference map is obtained which identifies differences between the two images and the colour difference map is converted into a pulse-phase difference map. A shutter-time difference map is obtained which identifies differences between capture times of corresponding locations in the two images. Using the shutter-time difference map, the pulse-phase difference map is corrected to obtain a map of pulse-phase changes which have occurred over a duration of a shutter scan.

20 Claims, 5 Drawing Sheets

Figure 1:
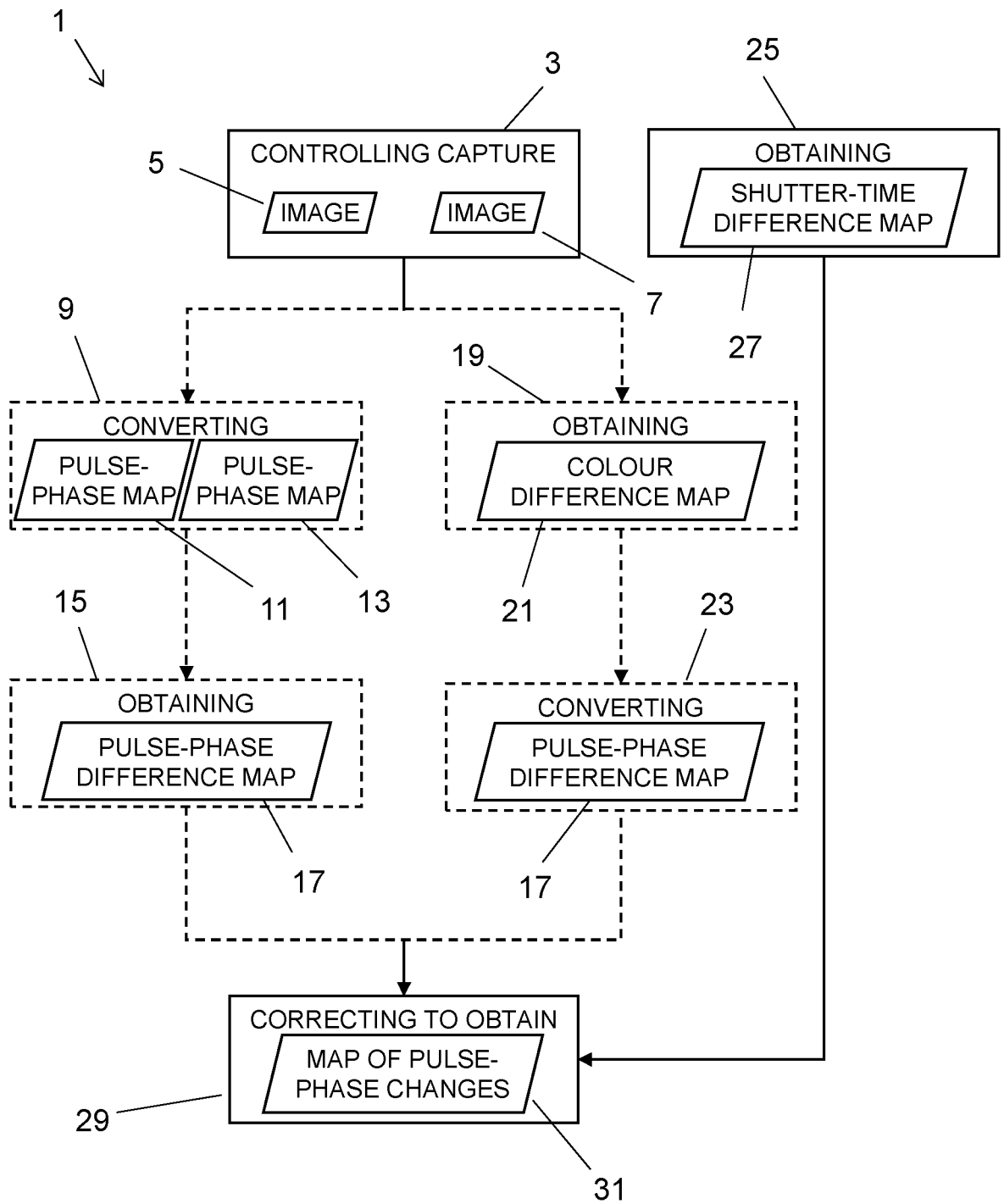

(51) Int. Cl.
　　　*A61B 5/103*　　　(2006.01)
　　　*H04N 23/73*　　　(2023.01)
　　　*G06V 10/74*　　　(2022.01)
　　　*H04N 23/45*　　　(2023.01)
　　　*H04N 23/58*　　　(2023.01)

(52) U.S. Cl.
　　　CPC .......... *H04N 23/58* (2023.01); *A61B 5/02416* (2013.01); *G06T 2207/10024* (2013.01); *G06T 2207/10144* (2013.01); *G06T 2207/30196* (2013.01)

(58) Field of Classification Search
　　　CPC ....... G03B 27/00; G02B 30/24; G01J 3/0232; G06V 10/74
　　　See application file for complete search history.

(56) References Cited

U.S. PATENT DOCUMENTS

| | | | |
|---|---|---|---|
| 10,044,939 B2* | 8/2018 | Flores | H04N 23/69 |
| 10,117,587 B2* | 11/2018 | Han | A61B 5/14552 |
| 10,352,853 B2* | 7/2019 | Shiono | A61B 5/4064 |
| 10,624,586 B2* | 4/2020 | Noguchi | A61B 5/7278 |
| 10,646,167 B2* | 5/2020 | De Haan | A61B 5/021 |
| 10,912,516 B2* | 2/2021 | Uchida | A61B 5/0077 |
| 11,412,943 B2* | 8/2022 | Misharin | A61B 5/02416 |
| 11,433,906 B2* | 9/2022 | Lu | B60W 50/14 |
| 11,545,048 B2* | 1/2023 | Otsuka | G06V 40/161 |
| 11,547,309 B2* | 1/2023 | Fukuda | A61B 5/02416 |
| 11,701,011 B2* | 7/2023 | Fukuda | A61B 5/02125 |
| | | | 600/485 |
| 2012/0114195 A1 | 5/2012 | Matsuda et al. | |
| 2016/0033738 A1* | 2/2016 | Kakkori | H04N 5/2628 |
| | | | 348/222.1 |
| 2016/0228011 A1* | 8/2016 | Tsubaki | A61B 5/024 |
| 2018/0168454 A1* | 6/2018 | Ando | A61B 5/0082 |
| 2020/0170512 A1* | 6/2020 | Ando | A61B 5/18 |
| 2020/0337573 A1 | 10/2020 | Fukuda et al. | |
| 2021/0267473 A1* | 9/2021 | Tomida | A61B 5/7278 |
| 2022/0197984 A1* | 6/2022 | Wright | G06N 5/01 |
| 2022/0294985 A1* | 9/2022 | Tomizawa | H04N 23/60 |
| 2022/0353444 A1* | 11/2022 | Robinson | H04N 25/531 |

FOREIGN PATENT DOCUMENTS

| | | |
|---|---|---|
| EP | 3968006 A1 | 3/2022 |
| WO | 2018/210985 A1 | 11/2018 |
| WO | 2019/122260 A1 | 6/2019 |

OTHER PUBLICATIONS

Wang et al., "Detail-preserving pulse wave extraction from facial videos using consumer-level camera", Biomedical Optics Express, vol. 11, No. 4, 2020, pp. 1876-1891.

Kamshilin et al., "Accurate measurement of the pulse wave delay with imaging photoplethysmography", Biomedical Optics Express, vol. 7, No. 12, 2016, pp. 5138-5147.

Kamshilin et al., "Alterations of blood pulsations parameters in carotid basin due to body position change", Scientific Reports, vol. 8. 2018, pp. 1-9.

"Vein Recognition Biometrics in BFSI Sector to Witness Robust Growth", Fact MR, Retrieved on Mar. 31, 2022, Webpage available at : https://www.factmr.com/report/1829/vein-recognition-biometrics-market.

"Aeon and Fujitsu pilot palm vein biometric payments", Finextra, Retrieved on Mar. 31, 2022, Webpage available at : https://www.finextra.com/newsarticle/32382/aeon-and-fujitsu-pilot-palm-vein-biometric-payments.

"Face ID might be using vein-matching tech to differentiate between twins", Apple Insider, Retrieved on Mar. 31, 2022, Webpage available at : https://appleinsider.com/articles/19/03/14/face-id-might-be-using-vein-matching-tech-to-differentiate-between-twins.

"Amazon Hand Recognition Could be the Future of Payments", Slash Gear, Retrieved on Mar. 31, 2022, Webpage available at : https://www.slashgear.com/amazon-hand-recognition-could-be-the-future-of-payments-21607268.

"Top-end 2020 iPhone to get larger camera sensor and sensor-shift stabilization", 9to5 Mac, Retrieved on Mar. 31, 2022, Webpage available at : https://9to5mac.com/2020/03/23/sensor-shift-stabilization/.

Mironenko et al., "Remote Photoplethysmography: Rarely Considered Factors", arXiv, Apr. 27, 2020, 10 pages.

Cotofana et al., "Can smiling influence the blood flow in the facial vein?—An experimental study", Journal of Cosmetic Dermatology, 2019, pp. 1-7.

Kumar et al., "DistancePPG: Robust non-contact vital signs monitoring using a camera", arXiv, Feb. 27, 2015, 24 pages.

Liu et al., "Toward a Smartphone Application for Estimation of Pulse Transit Time", Sensors, vol. 15, No. 10, 2015, pp. 27303-27321.

"3 Tips for Dealing With Rolling Shutter", The Beat, Retrieved on Mar. 31, 2022, Webpage available at : https://www.premiumbeat.com/blog/3-tips-for-dealing-with-rolling-shutter/.

"Amazon One: Palm scanner launched for 'secure' payments", BBC News, Retrieved on Mar. 31, 2022, Webpage available at : https://www.bbc.com/news/technology-54337984.

Extended European Search Report received for corresponding European Patent Application No. 21167919.6, dated Oct. 4, 2021, 5 pages.

* cited by examiner

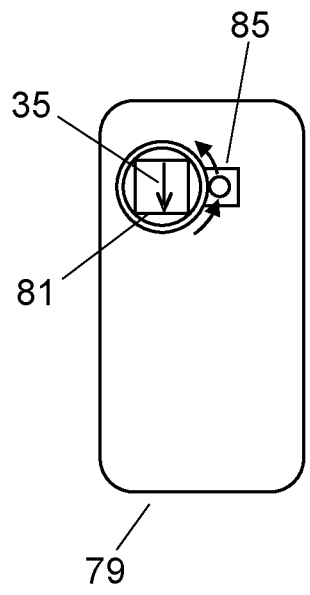
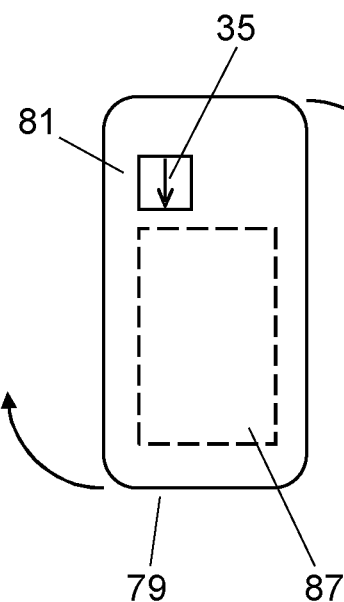
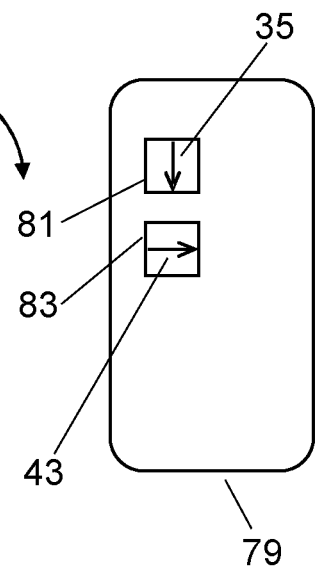
FIG 5A      FIG 5B      FIG 5C
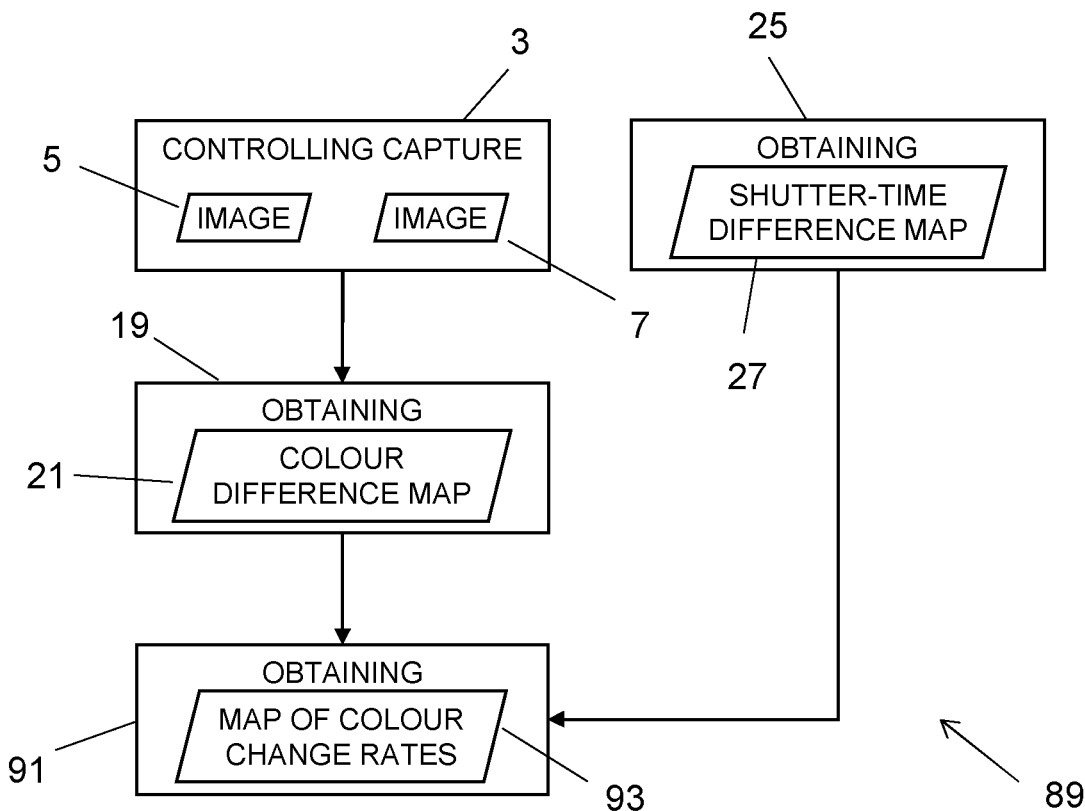
FIG 6

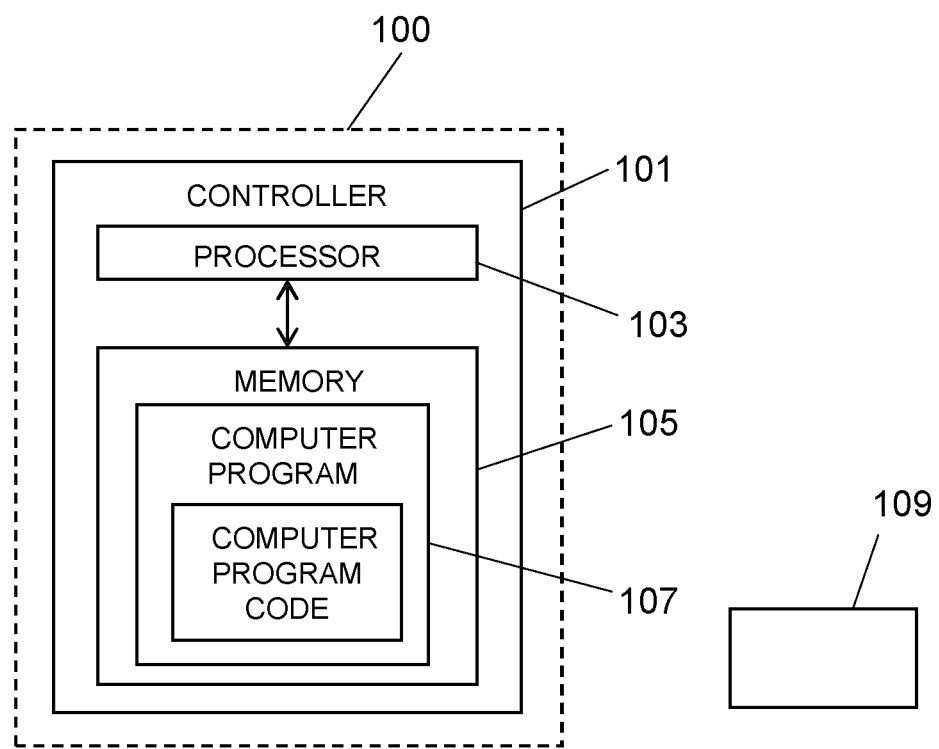
FIG 7                    FIG 8

MAPPING PULSE PROPAGATION

RELATED APPLICATION

This application claims priority to the European patent application number 21167919.6, filed on Apr. 12, 2021, the content of which is incorporated herein by reference in its entirety.

TECHNOLOGICAL FIELD

Embodiments of the present disclosure relate to mapping pulse propagation. Some relate to mapping the pulse propagation across an area which occurs within a duration of a shutter scan.

BACKGROUND

The propagation of a pulse across an area can be measured using measurements of the phase of the pulse at least at two different times. The ability to resolve the phase changes is limited by the frame rate of the camera. Additionally, if a rolling shutter camera is used, unknown phase changes will occur within the duration of the shutter scan.

BRIEF SUMMARY

According to various, but not necessarily all, embodiments there is provided an apparatus comprising means for: controlling capture of two images of an area, across which a pulse propagates, using different shutter scanning directions; converting the images into pulse-phase maps of the area; obtaining a pulse-phase difference map identifying differences between the pulse-phase maps of the area; obtaining a shutter-time difference map identifying differences between capture times of corresponding locations in the two images; and correcting the pulse-phase difference map using the shutter-time difference map to obtain a map of pulse-phase changes which have occurred over a duration of a shutter scan.

According to various, but not necessarily all, embodiments there is provided an apparatus comprising means for: controlling capture of two images of an area, across which a pulse propagates, using different shutter scanning directions; obtaining a colour difference map identifying differences between the two images; converting the colour difference map into a pulse-phase difference map; obtaining a shutter-time difference map identifying differences between capture times of corresponding locations in the two images; and correcting the pulse-phase difference map using the shutter-time difference map to obtain a map of pulse-phase changes which have occurred over a duration of a shutter scan.

According to various, but not necessarily all, embodiments there is provided an apparatus comprising means for: controlling capture of two images of an area, across which a pulse propagates, using different shutter scanning directions and beginning at the same time or an integer multiple of a pulse interval apart; obtaining a colour difference map identifying differences between the two images; obtaining a shutter-time difference map identifying differences between capture times of corresponding locations in the two images; and obtaining a map of colour change rates using the colour difference map and the shutter-time difference map, wherein colour change rates are indicative of pulse-phase changes which have occurred over a duration of a shutter scan.

According to various, but not necessarily all, embodiments there is provided a method comprising: controlling capture of two images of an area, across which a pulse propagates, using different shutter scanning directions; converting the images into pulse-phase maps of the area and obtaining a pulse-phase difference map identifying differences between the pulse-phase maps of the area, or obtaining a colour difference map identifying differences between the two images and converting the colour difference map into a pulse-phase difference map; obtaining a shutter-time difference map identifying differences between capture times of corresponding locations in the two images; and correcting the pulse-phase difference map using the shutter-time difference map to obtain a map of pulse-phase changes which have occurred over a duration of a shutter scan.

According to various, but not necessarily all, embodiments there is provided a computer program that, when run on a computer, performs: causing control of capture of two images of an area, across which a pulse propagates, using different shutter scanning directions; converting the images into pulse-phase maps of the area and obtaining a pulse-phase difference map identifying differences between the pulse-phase maps of the area, or obtaining a colour difference map identifying differences between the two images and converting the colour difference map into a pulse-phase difference map; obtaining a shutter-time difference map identifying differences between capture times of corresponding locations in the two images; and correcting the pulse-phase difference map using the shutter-time difference map to obtain a map of pulse-phase changes which have occurred over a duration of a shutter scan.

According to various, but not necessarily all, embodiments there is provided a non-transitory computer readable medium comprising instructions for performing at least the following or for causing an apparatus to perform at least the following: causing control of capture of two images of an area, across which a pulse propagates, using different shutter scanning directions; converting the images into pulse-phase maps of the area and obtaining a pulse-phase difference map identifying differences between the pulse-phase maps of the area, or obtaining a colour difference map identifying differences between the two images and converting the colour difference map into a pulse-phase difference map; obtaining a shutter-time difference map identifying differences between capture times of corresponding locations in the two images; and correcting the pulse-phase difference map using the shutter-time difference map to obtain a map of pulse-phase changes which have occurred over a duration of a shutter scan.

The following portion of this 'Brief Summary' section, describes various features that may be features of any of the embodiments described in the foregoing portion of the 'Brief Summary' section. The description of a function should additionally be considered to also disclose any means suitable for performing that function.

Controlling capture of the two images may comprise controlling timing of capture based on a pulse interval.

Controlling capture of the two images may comprise controlling timing of capture to follow capture of respective reference images of the area using the same shutter scanning direction after a delay of the same duration.

Controlling capture of the two images may comprise controlling timing of capture to substantially coincide with propagation of a target feature of a pulse waveform through a portion of the area which is of interest.

Controlling capture of the two images may comprise configuring settings of one or more of: an angle between the different shutter scanning directions; a shutter scanning speed; and a shutter aperture size. The one or more settings may be configured to achieve differences in capture times between a first subset of corresponding locations in the two images which are of greater duration than differences in capture times between a second subset of corresponding locations in the two images. The first subset represents a portion of the area which is of interest and the second subset represents another portion of the area.

Controlling capture of the two images may comprise configuring settings of one or more of: an angle between the different shutter scanning directions; a shutter scanning speed; and a shutter aperture size. The one or more settings may be configured based on a target difference in captures times between corresponding locations in the two images and/or a target duration of a shutter scan.

Obtaining a pulse-phase difference map from the two images may comprise using a stored periodic relationship between colour of the area and time to infer a pulse-phase from a colour.

Converting the two images into pulse-phase maps of the area may comprise generating two colour-difference maps, each identifying differences between the two images and respective reference images of the area captured using the same shutter scanning direction. Colour change rates may be used to identify pulse-phases at the time of the capture.

Correcting the pulse-phase difference map may comprise converting the shutter-time difference map to shutter-phase difference map. The conversion may be based on a pulse interval. The shutter-phase difference map may be subtracted from the pulse-phase difference map to correct the pulse-phase difference map.

One or more rotary actuators may be caused to rotate an image sensor to enable capture of the area using the different shutter scanning directions.

Provision of guidance to a user between capture of the two images may be caused. The guidance may indicate a manual rotation of an image sensor or the area which enables capture of the area using the different shutter scanning directions.

Capture of a second of the two images may be triggered in response to a determination of an orientation change between the area and an image sensor which enables capture of the area using the different shutter scanning directions.

Controlling capture of the two images may comprise triggering, at substantially the same time, capture using two image sensors having different shutter scanning directions.

Controlling capture of the two images may be triggered by an authentication request event.

According to various, but not necessarily all, embodiments there is provided examples as claimed in the appended claims. The scope of protection sought for various embodiments of the invention is set out by the independent claims. The examples and features, if any, described in this specification that do not fall under the scope of the independent claims are to be interpreted as examples useful for understanding various embodiments of the invention.

BRIEF DESCRIPTION

Figure 2:
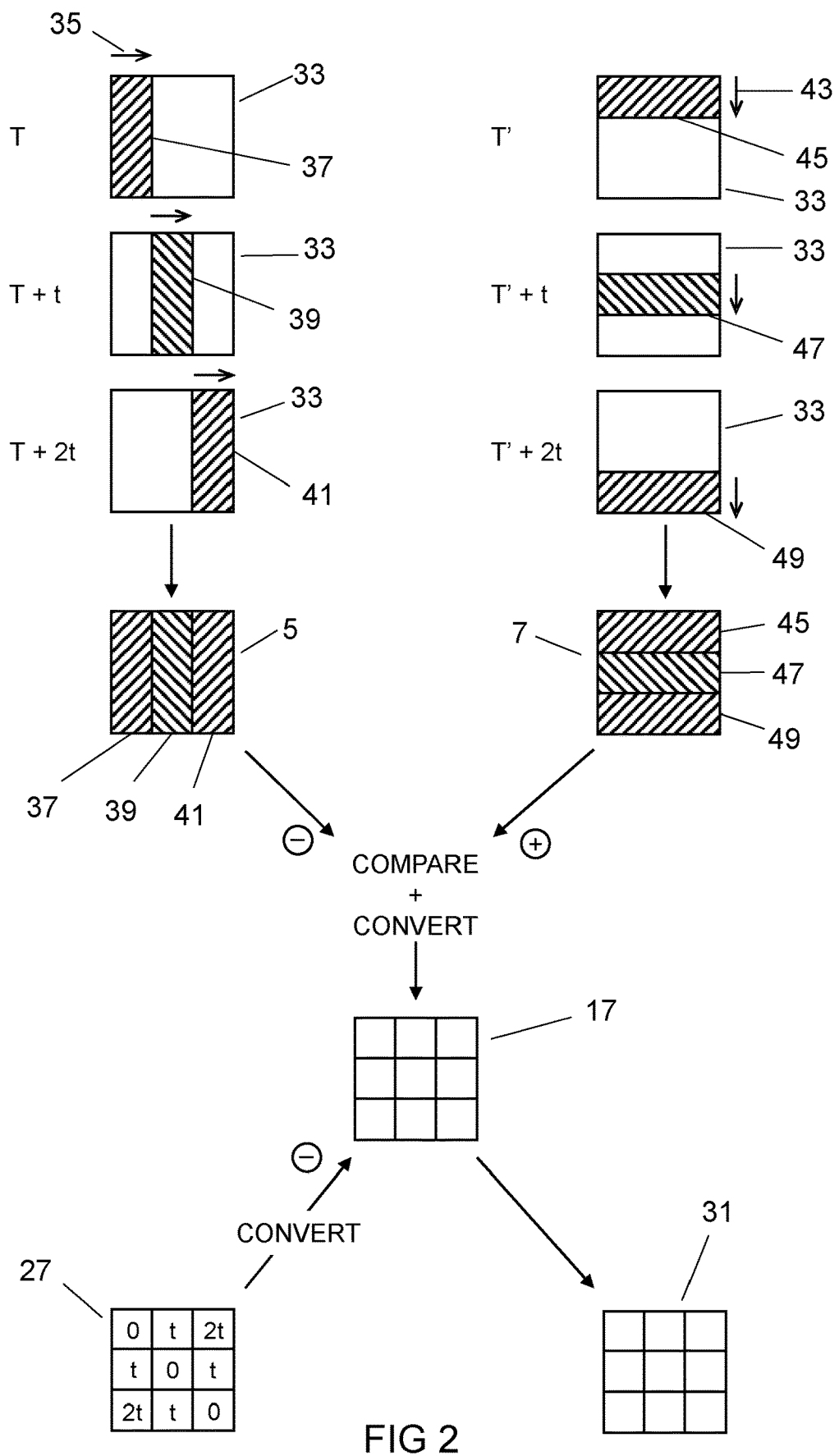
Figure 3:
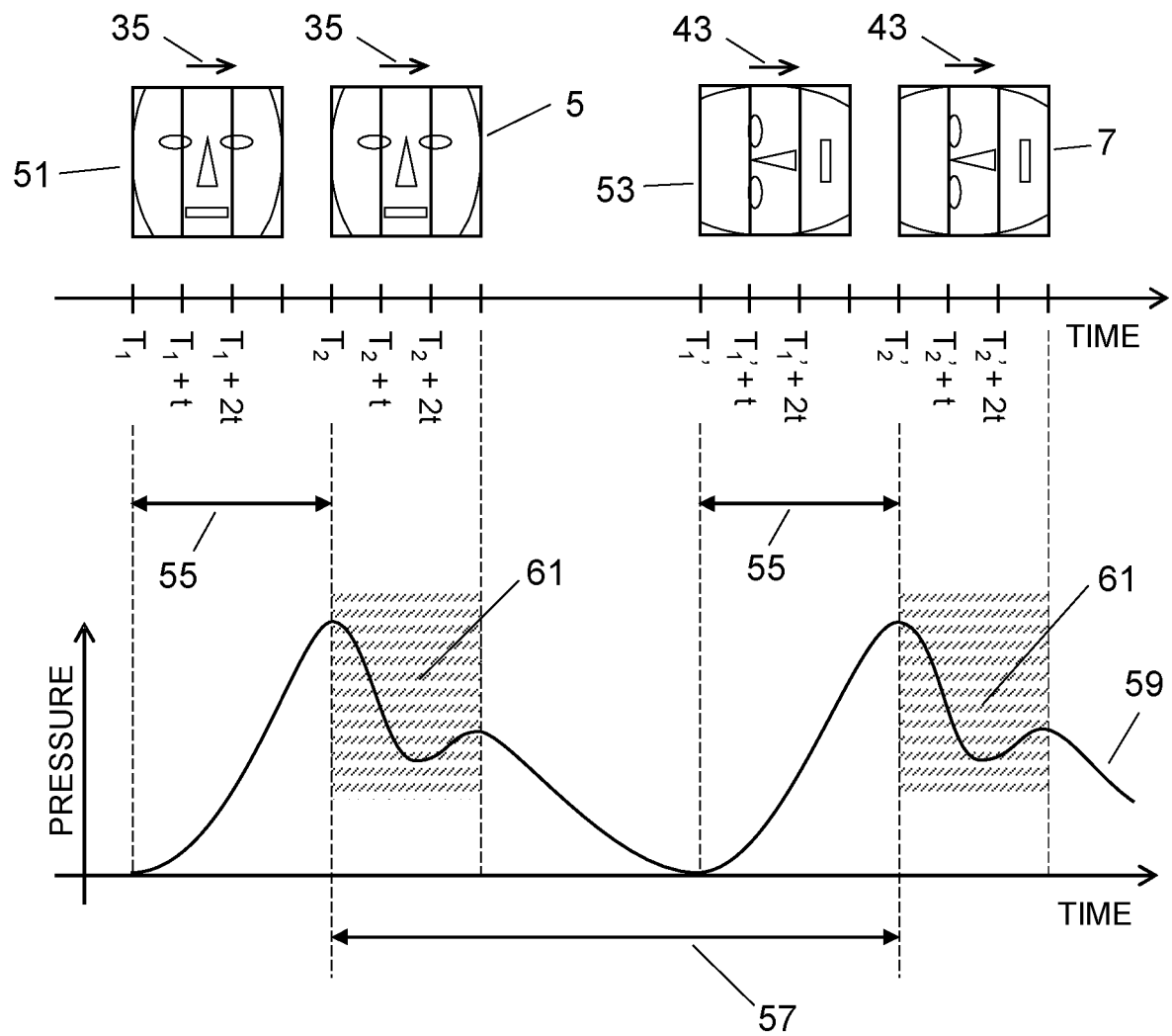
Figure 4:
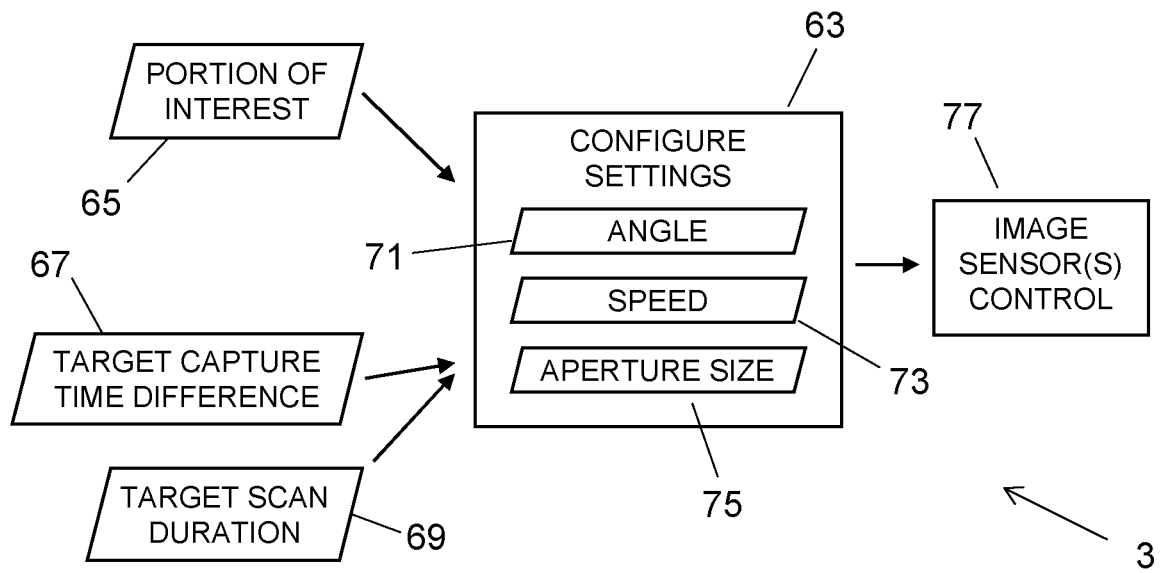

Some examples will now be described with reference to the accompanying drawings in which:
FIG. 1 shows an example method;
FIG. 2 illustrates the example method;
FIG. 3 shows example timings of image capture;
FIG. 4 shows examples of configuring settings for image capture;

FIGS. 5A to 5C show examples of achieving different shutter scanning direction for image capture;
FIG. 6 shows another example method;
FIG. 7 shows an example apparatus; and
FIG. 8 shows an example delivery mechanism for a computer program.

DETAILED DESCRIPTION

Examples of the disclosure relate to using images captured with different shutter scanning directions to resolve information about the pulse's propagation to within a duration of a shutter scan. The temporal resolution of information about the pulse's propagation is therefore dependent upon shutter scanning speed. Higher temporal resolution can be achieved by increasing the shutter scanning speed.

In some but not necessarily all examples described herein, the pulse is a blood pressure pulse in which the blood pressure rises and falls, responding to the cardiac cycle. Accordingly, the pulse is a periodic function, having a periodic waveform, and a phase of the pulse (pulse-phase) represents which stage of the cardiac cycle the blood pressure at a given location is responding to.

In some but not necessarily all examples described herein, the area through which the pulse's propagation is observed is a body surface, for example, a face or a palm, being formed of tissue and underlying vasculature and microvasculature (blood vessels) through which the blood flows.

The rising and falling of blood pressure causes changes in the volume of blood underlying the body surface. The changes in the volume of blood vary between individuals for reasons including differing spatial distributions of blood vessels and different distances of said blood vessels from the heart, where increased distance can increase the damping and timing of the pressure change. The changes in the volume of blood can also vary based on the emotional state (via hormone release) and health of the individual as these factors can affect the elasticity of the walls of the blood vessels and thus their resistance to changes in volume.

Accordingly, the pulse can be indicative of an individual or a health condition of an individual or an emotional state of an individual. Therefore, there may be many reasons to resolve information about the pulse's propagation. Reasons can include, for example, identification, health, and lie detecting. Examples of the present disclosure can find application in methods and apparatus relating to, for example, identification, health, and lie detecting.

The changes in the volume of blood underlying the body surface result in colour changes over the period of the cardiac cycle. Therefore, the changes in volume can be detected by detecting the colour changes. The colour changes can be detected in the reflectance or absorbance of light by the body surface.

Despite the foregoing, it is to be appreciated that the methods and apparatus herein described can be used to resolve information about other pulse signals propagating across other areas such as, for example, other pulse signals that cause periodic optical changes, including periodic colour changes, in the area across which they propagate.

FIG. 1 shows an example method 1 for obtaining spatio-temporal information about an evolution of the pulse. The spatio-temporal information obtained is in the form of a map 31 of pulse-phase changes which have occurred over a duration of a shutter scan. Method 1 is described also with reference to FIG. 2, which illustrates the blocks in the method that are shown in FIG. 1.

At block 3, method 1 comprises controlling capture of two images 5, 7 of an area 33, across which the pulse propagates, using different shutter scanning directions 35, 43.

The shutter scanning successively exposes parallel linear spans of sensels (discrete photosites) of an image sensor used to capture one or both images 5, 7 of the area 33. The shutter may be a mechanical shutter, wherein light is incident on only those linear spans of sensels aligned with the shutter aperture. The shutter may be an electronic (virtual) shutter, wherein light may be incident on all sensels while, at a given time, signals are only read out from a subset formed in a linear span.

Capture of the two images 5, 7 using different shutter scanning directions 35, 43 is illustrated in FIG. 2.

A first image 5 is captured using a first shutter scanning direction 35. A first portion 37 of the area 33 is captured at time T, a second portion 39 at a time T+t, and a third portion 41 at time T+2t. The combination of these three portions 37, 39, 41 produces the first image 5. It will be appreciated that the first image 5 may be produced by the combination of more than three successively captured portions.

A second image 7 is captured using a second shutter scanning direction 43. A fourth portion 45 of the area 33 is captured at a time T' (time T and time T' may be the same or different), a fifth portion 47 at time T'+t, and a sixth portion 49 at time T'+2t. The combination of these three portions 45, 47, 49 produces the second image 7. It will be appreciated that the second image 7 may be produced by the combination of more than three successively captured portions.

The second shutter scanning direction 43 is different to the first shutter scanning direction 35. The first and second shutter scanning directions 35, 43 are different directions relative to the area 33. They may not be different directions relative to an image sensor. For example, if a mechanical shutter having a fixed scanning direction relative to an image sensor is utilized to perform the shutter scan and the image sensor is rotated relative to the area 33 between capture of the first image 5 and the capture of the second image 7, then the first and second shutter scanning directions 35, 43 will be different directions relative to the area 33. In other examples they may be different directions also relative to the image sensor. For example, if an image sensor used to capture the first and second images 5, 7 utilizes an electronic (virtual) shutter, then the first and second shutter scanning directions 35, 43 can also be different directions relative to the image sensor.

The two images 5, 7 can be captured using substantially the same shutter scanning speed and substantially the same shutter aperture width.

The two images 5, 7 can be captured as frames of a video.

In some examples, controlling capture of the two images 5, 7, and hence method 1 as a whole, can be triggered by an authentication request event. Controlling capture of the two images 5, 7 may, in other examples, be triggered by other trigger events such as, for example, a user input to a device on which method 1 is performed or a request from one or more applications run on that device. Requests may be made by any application for which high temporal resolution of a pulse's propagation within the area 33 will be beneficial.

In some examples, images of the area 33 can be captured using more than just two different shutter scanning directions. For example, one or more images may be captured using one or more shutter scanning directions which are oriented between the first and second shutter scanning directions 35, 43. For example, where the first and second shutter scanning directions 35, 43 differ by 90 arc degrees, a third image can be captured using a shutter scanning direction that differs from the first and second shutter scanning directions 35, 43 by 45 arc degrees. Images such as this third image provide repeat measurements and therefore noise reduction.

Method 1 comprises obtaining a pulse-phase difference map 17 from the two images 5, 7. Two alternatives for obtaining the pulse-phase difference map 17 are herein described. These alternatives are shown by two parallel paths, using dashed lines, in FIG. 1. Both alternatives involve an element of comparing and converting colour values to pulse-phase values, although it is to be appreciated that in other examples other image features besides colour may be indicative of pulse-phase and thus may be used in reparameterising the two images 5, 7, or derivatives thereof, into the pulse-phase domain.

In the first alternative (left-hand path shown in FIG. 1), method 1 comprises blocks 9 and 15.

At block 9, method 1 comprises converting the images 5, 7 into pulse-phase maps 11, 13 of the area 33. The pulse-phase maps 11, 13 differ from one another. Pulse-phase has a spatio-temporal distribution in the area 33. The area 33 is captured according to different temporal distributions as a result of the different shutter scanning directions 35, 43. Therefore, different spatial distributions of pulse-phase within the area 33 will be recorded (via colour differences) in the two images 5, 7.

In some examples, converting the images 5, 7 into pulse-phase maps 11, 13 comprises using a stored periodic relationship between the colour of the area 33 and time to infer a pulse-phase from a colour. The stored period relationship can be generic to the class or sub-class of area to which the area 33 belongs. For example, where the area 33 is a face, the stored periodic relationship may be generic to faces or may be generic to faces but, for example, age-matched. The stored periodic relationship can be specific to the area 33. For example, the stored periodic relationship may have been captured during the propagation of a prior pulse across the area 33.

In some examples, the pulse-phase within the pulse-phase map 11 can be normalised by subtracting the minimum pulse-phase value derived from the first image 5 from the pulse-phase values at each location so that the pulse-phase map 11 identifies the relative pulse-phases between the mapped locations. The pulse-phase map 13 can likewise be normalised by subtracting the minimum pulse-phase value derived from the second image 7 from the pulse-phase values at each location so that the pulse-phase map 13 identifies the relative pulse-phases between the mapped locations.

In some examples, the pulse-phase within the pulse-phase map 11 can be normalised by subtracting the average, for example mean average, pulse-phase value derived from the first image 5 from the pulse-phase values at each location so that the pulse-phase map 11 identifies the relative pulse-phases between the mapped locations. The pulse-phase map 13 can likewise be normalised by subtracting the average, for example mean average, pulse-phase value derived from the second image 7 from the pulse-phase values at each location so that the pulse-phase map 13 identifies the relative pulse-phases between the mapped locations.

At block 15, method 1 comprises obtaining the pulse-phase difference map 17 identifying differences between the pulse-phase maps 11, 13 of the area 33. Differences between the pulse-phase maps 11, 13 may be identified by subtracting pulse-phase values at corresponding locations in the pulse-phase maps 11, 13. "Corresponding locations" refer to the same sub-portion of the area 33. That is: a pulse-phase value for a sub-portion of the area 33 as recorded in one of the pulse-phase maps 11, 13 is subtracted from the pulse-phase value for the same sub-portion of the area 33 as recorded in the other of the phase-maps 11, 13 in order to obtain a pulse-phase difference value for that sub-portion of the area 33 which is to be recorded in the pulse-phase difference map 17, which records pulse-phase difference values for all sub-portions of the area 33.

In the second alternative (right-hand path shown in FIG. 1), method 1 comprises blocks 19 and 23.

At block 19, method 1 comprises obtaining a colour difference map 21 identifying differences between the two images 5, 7. Differences between images 5, 7 may be identified by subtracting colour values of corresponding locations in the two images 5, 7. Each sensel of an image sensor captures a sub-portion of the area 33 as a pixel in respective images 5, 7. "Corresponding locations in the two images 5, 7" refers to the same sub-portion of the area 33, not to the same pixel position, although this may be also true if the images 5, 7 are suitably aligned.

At block 23, method 1 comprises converting the colour difference map 21 into a pulse-phase difference map 17. In some examples this conversion uses the stored periodic relationship between the colour of the area 33 and time, described with reference to block 9, to infer pulse-phase from colour.

At block 25, method 1 comprises obtaining a shutter-time difference map 27 identifying differences between capture times of corresponding locations in the two images 5, 7. As in the foregoing, "corresponding locations in the two images 5, 7" refers to the same sub-portion of the area 33. Capture times can be considered relative to the beginning of the capture of respective images. Capture times may be expressed as positive time differences relative to the earliest time that a pixel is captured such as, for example, time T for the first image 5 and time T' for the second image 7.

FIG. 2 illustrates an example shutter-time difference map 27 in which the angle between the different shutter scanning directions 35, 43 is 90 arc degrees. The corresponding locations along a central diagonal such as, for example, from top-left to bottom-right, would be captured at the same time relative to respective beginnings of the capture and thus the differences in the capture time between these corresponding locations are zero. In the example illustrated in FIG. 2 with the images 5, 7 being composed each of three portions captured at different times, a greatest difference in capture time comes for those sub-portions of the area 33 which are part of both the first and sixth portions 37, 49 of the area 33 or a part of both the third and fourth portions 41, 45 of the area 33. For these corresponding locations the capture time differences are 2t. As will therefore be appreciated, the shutter-time difference map 27 is dependent on the angle between the different shutter scanning directions 35, 43 and shutter settings such as shutter scanning speed and shutter aperture size. Therefore, in some examples where the angle and shutter settings are fixed or use a preset configuration, obtaining the shutter-time difference map 27 can comprise retrieval of a stored version from a memory. In other examples, the shutter-time difference map 27 can be calculated from the angle and shutter settings.

At block 29, method 1 comprises correcting the pulse-phase difference map 17 using the shutter-time difference map 27 to obtain a map 31 of pulse-phase changes which have occurred during the duration of a shutter scan. The duration of a shutter scan is the time taken to capture a single image using rolling shutter image capture. It is the time taken for the shutter to scan across the image sensor, exposing each of the sensels for a given exposure time.

In some examples, correcting the pulse-phase difference map 17 comprises converting the shutter-time difference map 27 into a shutter-phase difference map. This conversion is based on a pulse interval; that is: on the period of the cardiac cycle. For an average human at rest, this is around 1 second. A phase difference can be considered as representing a proportion of the period of a periodic function. Thus, a time can be converted to a pulse-phase difference using the pulse interval. Differences in capture times for corresponding locations in the images 5, 7 can be converted to pulse-phase differences using the pulse interval. The resultant shutter-phase difference map represents the pulse-phase difference that would be seen between the pulse-phase maps 11, 13 (or between the two images 5, 7 if they were converted into pulse-phase maps) if the pulse-phase at each location within the area 33 changed in the same way. However, the pulse at each location within the area 33 has a different evolution due to, for example, differences in the underlying vasculature and/or microvasculature, and thus does not change in the same way. Hence, by subtracting the shutter-phase difference map from the pulse-phase difference map 17, what remains is a map 31 of the pulse-phase changes which occurred within the area 33 due to the pulse's evolution during the duration of the shutter scan.

The respective order of blocks 15 or 23 and block 29 in method 1 shown in FIG. 1 should not be understood as requiring them to be performed entirely successively. The obtaining and correcting of the pulse-phase difference map 17 may be performed substantially contemporaneously by, for example, obtaining and correcting the pulse-phase difference for each corresponding location in the image 5, 7 in turn or by any other means of incrementally or progressively obtaining the map 31 of pulse-phase changes.

FIG. 3 illustrates a number of examples of how timing of the capture of the two images 5, 7 can be controlled. Controlling the timing of capture can be an aspect of controlling the capture at block 3 of method 1.

In some examples, the timing of the capture of the two images 5, 7 can be based on the timing of capture of respective reference images 51, 53. Block 3 of method 1 can comprise controlling timing of capture of the two images 5, 7 to follow capture of respective reference images 51, 53 of the area 33, using the same shutter scanning direction, after a delay 55 of the same duration. That is, the time of capture of the first image 5 follows capture of a first referenced image 51 after a delay 55. The first image 5 is captured using the same shutter scanning direction 35 as the first referenced image 51. The time of capture of the second image 7 follows capture of a second referenced image 53 after a delay 55 of the same duration (the interval between times $T_1$ and $T_2$ is the same as between times $T_1'$ and $T_2'$). The second image 7 is captured using the same shutter scanning direction 43 as the second referenced image 53.

The reference images 51, 53 can be captured using substantially the same shutter scanning speed and substantially the same shutter aperture width as are used to capture the images 5, 7.

Although FIG. 3 shows the capture of both the first reference image 51 and the first image 5 before the capture of the second reference image 53 and the second image 7 (the interval between times $T_1$ and $T_1'$ is greater than between times $T_1$ and $T_2$), it will be appreciated that the two reference images 51, 53 can be captured before either of the two images 5, 7. For example, the order of capture can be as follows: the first reference image 51, the second reference image 53, the first image 5, and then the second image 7 (the interval between times $T_1$ and $T_1'$ can be less than the interval between times $T_1$ and $T_2$). This involves the changing of the shutter scanning direction between each image capture. Alternatively, the first and second reference images 51, 53 can be captured at substantially the same time (time $T_1$ and $T_1'$ can be the same), followed by the first and second images 5, 7 captured at substantially the same time (time $T_2$ and $T_2'$ can be the same).

The referenced images 51, 53 can be used to account for differences in the pulse-phases at the time when the respective captures of the images 5, 7 begin. This allows the two images 5, 7 to be captured within a single pulse interval 57 (within a single cardiac cycle). The converting of the two images 5, 7 into pulse-phase maps 11, 13 of the area 33, as per block 9 of method 1, can comprise generating two colour difference maps, each identifying differences between the two images 5, 7 and respective reference images 51, 53 of the area 33 captured using the same shutter scanning direction. Colour change rates can be determined using the colour difference maps and the delay 55. The colour change rates can be used to identify pulse-phases at the time of capture of the two images 5, 7. Using colour change rates rather than colour values to perform the conversion to the pulse-phase domain may result in lower noise.

An example of a temporal relationship between the timing of capture of the images 5, 7 and an evolution (waveform 59) of a pulse at, for example, a portion of the area 33 which is of interest is shown also in FIG. 3.

In some examples, the timing of capture can be based on the pulse interval 57. The initiation of capture and shutter scanning in respect of the first image 5 can be followed after a delay, equal in duration to the pulse interval 57, by the initiation of capture and shutter scanning in respect of the second image 7. It is to be appreciated that the captures may begin another integer multiple of the pulse interval 57 apart. Thus, block 3 of method 1 can comprise, in some examples, controlling capture of the two images 5, 7 so that the captures begin an integer multiple of the pulse interval 57 apart. By beginning the captures an integer multiple of the pulse interval 57 apart, the captures will begin at the same pulse-phases enabling the images 5, 7 (or derivatives of them such as the pulse-phase maps 11, 13) to be compared directly. In some such examples, referenced images 51, 53 may not be captured.

In some examples, the timing of capture can be based on a target feature 61 of the pulse waveform 59. Block 3 of method 1 can comprise controlling the timing of capture of one or more of the two images 5, 7 to substantially coincide with propagation of a target feature 61 of a pulse waveform 59 through a portion of the area 33 which is of interest. In some examples, to enable capture to be timed to coincide with the target feature 61, the timing of the target feature 61 may be determined from observation of a colour change in the portion, which is characteristic of the target feature 61, in a prior colour change cycle and capture of images 5, 7 may be performed at any integer multiple of the pulse interval 57 thereafter. The target feature 61 may be a feature of the pulse waveform 59 which enables more accurate phase recognition. An example of such a feature is the dicrotic notch, which is labelled as the target feature 61 in FIG. 3.

The timing of capture can be based on one or both of the pulse interval 57 and the target feature 61 of the pulse waveform 59.

In some examples, the timing of capture of the images 5, 7 specifically may not be controlled. Instead, the images 5, 7 (and reference images 51, 53, if used) can be selected from a sequence of frames obtained by video capture.

The primary selection criterium may be the shutter scanning direction with which the frames are captured. For example, if only one frame is captured using the first shutter scanning direction 35, then this frame will be selected as the first image 5 and if only one frame is captured using the second shutter scanning direction 43, then this frame will be selected as the second image 7.

Secondary selection criteria can include the timing considerations described with reference to FIG. 3 above.

For example, where multiple frames are captured using the first shutter scanning direction 35, one of these frames which also substantially coincides with propagation of a target feature 61 of a pulse waveform 59 through a portion of the area 33 which is of interest may be selected as the first image 5. Likewise, where multiple frames are captured using the second shutter scanning direction 43, one of these frames which also substantially coincides with propagation of a target feature 61 of a pulse waveform 59 through a portion of the area 33 which is of interest may be selected as the second image 7.

The first and second image 5, 7 can be selected from pairs of frames (in the event that there is more than one pair) which are both respectively captured using the first and second shutter scanning directions 35, 43 and are captured an integer multiple of the pulse interval 57 apart.

From amongst those frames captured using the first shutter scanning direction 35, a pair of frames with a delay 55 between their respective captures can be selected as the first reference image 51 and the first image 5 if, amongst those frames captured using the second shutter scanning direction 43, there is a pair of frames which have the same delay 55 between their respective captures. That pair of frames, from amongst those captured using the second shutter scanning direction 43, can be selected as the second reference image 53 and the second image 7.

FIG. 4 illustrates examples of configuring capture-related settings. Examples of capture-related settings can include, for example: an angle 71 between the different shutter scanning directions 35, 43; a shutter scanning speed 73; and a shutter aperture size 75. In the examples of FIG. 4, the settings of one or more of these can be configured. The controlling of the capture of images 5, 7 at block 3 of method 1 can be based on the settings which result. Thus, blocks 63 and 77 illustrated in FIG. 4 may be sub-blocks of block 3.

In some examples, at block 63, method 1 comprises configuring settings of one or more of: an angle 71 between the different shutter scanning directions 35, 43; a shutter scanning speed 73; and a shutter aperture size 75, to achieve differences in capture times between a first subset of corresponding locations in the two images 5, 7 which are of greater duration than differences in capture times between a second subset of corresponding locations in the two images 5, 7. In these examples, the first subset represents a portion 65 of the area 33 which is of interest and the second subset represents another portion of the area 33. Portions 65 of the area 33 of interest can include those which have underlying vasculature and/or microvasculature which is sufficiently distinctive to enable identification of the user for authorization purposes. A record of such portions 65 may be stored in a memory and retrieved for the purpose of configuring the settings of capture-related parameters. The portions 65 of the area 33 which are known to be of interest may be recognised from a live image of the area 33 using, for example, computer vision.

In some examples, at block 63, method 1 comprises configuring settings based on a target difference in capture times (target capture-time difference 67) between corresponding locations in the two images 5, 7 and/or a target duration 69 of a shutter scan.

The target capture-time difference 67 may be for at least a subset of the corresponding locations and not necessarily for all corresponding locations. Said subset may be the aforementioned first subset representing a portion 65 of the area 33 which is of interest. The target capture-time difference 67 provides for sufficient colour contrast between corresponding locations to enable the pulse-phase to be accurately resolved. Therefore, the target capture-time difference 67 may be based on the sensitivity of the image sensor to differences in colour and may also be based upon current lighting conditions.

The target duration 69 of a shutter scan can be based on a target temporal resolution of pulse-phase changes. In configuring the settings, it may be acceptable to exceed this target meaning that a shorter duration of the shutter scan than the target duration 69 and thus a higher temporal resolution than the target temporal resolution can be obtained.

In some examples the target capture-time difference 67 and the target duration 69 of the shutter scan can be conflicting. For example, it may be possible to achieve the target capture-time difference 67 only if the duration of the shutter scan is longer than the target duration 69. Therefore, configuring settings, as at block 63, can comprise an optimization taking one or both of the target capture-time difference 67 and the target duration 69 of the shutter scan as soft constraints, where it is not essential that the targets are met but failure to satisfy them and the extent to which they are not satisfied is penalized in the optimization.

FIGS. 5A to 5C illustrate examples of how the different shutter scanning directions 35, 43 can be achieved.

Each of FIGS. 5A to 5C show images sensors 81 (and 83) comprised in a device 79. The image sensors 81 (and 83) can be sensitive to visible or infrared light. The image sensors 81 (and 83) can be rolling shutter image sensors. The shutter can be a mechanical shutter or an electronic (virtual) shutter. The image sensors 81 (and 83) may be configured to capture video. The device 79 can be an electronic device. It can be portable, such as a user device, or fixed to a structure, such as a building or vehicle.

In the example of FIG. 5A, to enable capture of the area 33 using the different shutter scanning directions 35, 43 using a single image sensor 81, the image sensor 81 is rotated with respect to the device 79 in which it is comprised. For example, the device 79 can comprises one or more rotary actuators 85 configured to rotate the image sensor 81. The image sensor 81 may be rotated around an optical axis of a lens associated with the image sensor 81.

Therefore, even if the shutter scanning direction is fixed with respect to the image sensor 81, by rotating the image sensor 81 with respect to the device 79, the shutter scanning direction for capturing different images can be changed whilst the device 79 is maintained in its position relative to the area 33 to be imaged.

Method 1 can therefore comprise causing one or more rotary actuators 85 to rotate an image sensor 81 to enable capture of the area 33 using the different shutter scanning directions 35, 43.

The use of one or more rotary actuators 85 to rotate an image sensor 81 enables relatively rapid re-orientation of the shutter scanning direction. For example, the one or more rotary actuators 85 may be configured to rotate the image sensor 81 through 270 arc degrees or more within a single pulse interval 57, which, for an average human at rest, is around 1 second. The example of FIG. 5A is therefore suitable for implementing method 1 where the shutter scanning directions is changed between each image capture. For example, the example of FIG. 5A is suitable for capturing the first reference image 51, the second reference image 53, the first image 5, and the second image 7 in that order within a single pulse interval 57. Capturing these images within a single pulse interval 57 can result in lower noise in the map 31 of pulse-phase changes.

In the example of FIG. 5B, the image sensor 81 is not rotatable with respect to the device 79 in which it is comprised. The shutter scanning direction is fixed relative to the image sensor 81. To enable capture of the area 33 using the different shutter scanning directions 35, 43, the device 79 can be rotated with respect to the area 33 to be imaged. The device 79 can comprise a user interface 87 configured to provide guidance to a user between capture of the two images 5, 7. The guidance indicates a manual rotation of the image sensor 81 (by means of manual rotation of the device 79 in which it is comprised) or the area 33 which enables capture of the area 33 using the different shutter scanning directions 35, 43.

The guidance can comprise visual features in examples where the user interface 87 is a display or aural features in examples where the user interface 87 is a speaker.

The guidance can guide the user to move the device 79 continuously through a rotational arc which changes the orientation of the image sensor 81 relative to the area 33 but which minimises movement of the image sensor's position in space.

Alternatively, the guidance may indicate one or multiple orientations for the user to effect between the device 79 (and image sensor 81) and the area 33 without providing guidance on how to move the device 79 between these orientations.

The guidance may also guide the user to rotate the area 33 with respect to the device 79 so that the device 79 can remain static. For example, the user may be guided to tilt their head to rotate their face relative to the device 79 or to rotate a palm relative to the device 79 in examples where, respectively, the area 33 to be imaged is the user's face or palm.

Method 1 can therefore comprise causing provision of guidance to the user between capture of the two images 5, 7, the guidance indicating a manual rotation of an image sensor 81 or the area 33 which enables capture of the area 33 using the different shutter scanning directions 35, 43.

In the examples of FIGS. 5A and 5B, the capture of the second image 7 (or whichever of the two images 5, 7 is captured later) can be triggered in response to a determination of an orientation change between the area 33 and the image sensor 81 which enables capture of the area 33 using the different shutter scanning directions 35, 43 or using substantially the different shutter scanning directions 35, 43, where the angle between the actual shutter scanning directions is within a tolerance threshold of the angle 71 set by block 63 of method 1. In the example of FIG. 5A, this determination can comprise detecting the completion of the rotation of the image sensor 81 through the angle between the targeted shutter scanning directions 35, 43 by the one or more rotary actuators 85. In the example of FIG. 5B, this determination can comprise detecting the manual rotation has been completed using, for example, accelerometers, gyroscopes, and/or magnetometers of the device 79 or, for example, processing live image data to recognise that the orientation of features in the area 33 has changed by the angle between the targeted shutter scanning directions 35, 43.

Alternatively, the two images 5, 7 can be captured by a single image sensor 81 using the different shutter scanning directions 35, 43 without relative rotation between the image sensor 81 and the area 33 if the image sensor 81 utilises an electronic (virtual) shutter.

In the example of FIG. 5C, two image sensors 81, 83 enable capture of the two images 5, 7 at substantially the same time. The two image sensors 81, 83 are comprised in the device 79 and have, at least at the time of capture, different shutter scanning directions 35, 43. They may either be fixed with different shutter scanning directions or one or both could be rotatable with respect to the device 79 in the manner as described with reference to FIG. 5A. Alternatively, if the two image sensors 81, 83 utilise electronic (virtual) shutters, then there is no need for either the image sensor 81 or the image sensor 83 to be rotated.

Method 1 can therefore comprise triggering, at substantially the same time, capture using two image sensors 81, 83 having, at least at the time of capture, different shutter scanning directions 35, 43.

The examples hereinbefore described have involved a conversion, for example at block 9 or block 23, between colour (or other optical features) and pulse-phase. Converting measurements into pulse-phase enables comparison with measurements taken at different stages in the cardiac cycle. This means that method 1 can use images 5, 7 that have been captured within a single cycle. However, in the examples where the two images 5, 7 are captured at the same time (for example, by using two image sensors as described with reference to FIG. 5C) or an integer multiple of the pulse interval 57 apart, conversion between colour and pulse-phase can be omitted. FIG. 6 shows an example method 89 which omits the conversion.

At block 3, the method 89 comprises controlling capture of two images 5, 7 of an area 33, across which a pulse propagates, using different shutter scanning directions 35, 43. In method 89, controlling capture of the two images 5, 7 further comprises beginning the captures at the same time or an integer multiple of the pulse interval 57 apart. The controlling of the capture of the two images 5, 7 can otherwise be the same as described in any of the foregoing examples described with reference to method 1. For example, the timing of the capture can be controlled to substantially coincide with propagation of a target feature 61 of a pulse waveform 59 through a portion 65 of the area 33 which is of interest as described with reference to FIG. 3. For example, the settings of one or more of: an angle 71 between the different shutter scanning directions 35, 43; a shutter scanning speed 73; and a shutter aperture size 75, can be configured as described with reference to FIG. 4. For example, the different shutter scanning directions 35, 43 can be achieved as described with reference to any of FIGS. 5A to 5C.

At block 19, method 89 comprises obtaining a colour difference map 21 identifying differences between the two images 5, 7. The obtaining of the colour difference map 21 can be the same as described in any of the foregoing examples described with reference to method 1.

At block 25, method 89 comprises obtaining a shutter-time difference map 27 identifying differences between capture times of corresponding locations in the two images 5,7. The obtaining of the shutter-time difference map 27 can be the same as described in any of the foregoing examples described with reference to method 1.

At block 91, the method 89 comprises obtaining a map 93 of colour change rates using the colour difference map 21 and the shutter-time difference map 27. Colour change rates are indicative of pulse-phase changes which have occurred over a duration of a shutter scan.

In some examples, the average, for example mean average, colour change rate is subtracted from the colour change rate at each mapped location in the map 93 of colour change rates to obtain a map of relative colour change rates. In other examples, the minimum colour change rate is subtracted from the colour change rate at each mapped location in the map 93 of colour change rates to obtain a map of relative colour change rates. Subtraction of the average colour change rate may be preferred over subtraction of the minimum colour change rate as it is less susceptible to high frequency or single pixel noise.

Because colour change rates are indicative of pulse-phase changes, at least some applications which use the map 31 of pulse-phase changes can be adapted to use the map 93 of colour change rates or map of relative colour change rates. For example, authentication can be performed using colour change rates. For example, authentication can be performed using the colour change rates from map 93, the relative colour change rates as between different mapped locations, differences in colour change rates between portions of the area 33 mapped, or variations of the colour change rates over time.

Omitting the conversion between colour and pulse-phase can be advantageous where there is, for example, a lack of available information on a periodic relationship between colour of the area 33 and time or to avoid introducing estimation errors which may result from the use of an available relationship to infer pulse-phase.

FIG. 7 illustrates an example of an apparatus 100. The apparatus 100 may be a chip or a chip-set. The apparatus 100 may be or be comprised in the device 79.

In the example of FIG. 7 the apparatus 100 comprises a controller 101. Implementation of a controller 101 may be as controller circuitry. The controller 101 may be implemented in hardware alone, have certain aspects in software including firmware alone or can be a combination of hardware and software (including firmware).

As illustrated in FIG. 7 the controller 101 may be implemented using instructions that enable hardware functionality, for example, by using executable instructions of a computer program 107 in a general-purpose or special-purpose processor 103 that may be stored on a computer readable storage medium (disk, memory etc) to be executed by such a processor 103.

The processor 103 is configured to read from and write to the memory 105. The processor 103 may also comprise an output interface via which data and/or commands are output by the processor 103 and an input interface via which data and/or commands are input to the processor 103.

The memory 105 stores a computer program 107 comprising computer program instructions (computer program code) that controls the operation of the apparatus 100 when loaded into the processor 103. The computer program instructions, of the computer program 107, provide the logic and routines that enables the apparatus to perform the methods illustrated in, or described with reference to, any preceding FIG. The processor 103 by reading the memory 105 is able to load and execute the computer program 107.

In some examples, the apparatus 100 therefore comprises:
at least one processor 103;
and at least one memory 105 including computer program code. The at least one memory 105 and the computer program code are configured to, with the at least one processor 103, cause the apparatus 100 at least to perform:

controlling 3 capture of two images 5, 7 of an area 33, across which a pulse propagates, using different shutter scanning directions 35, 43;

converting 9 the images 5, 7 into pulse-phase maps 11, 13 of the area 33;

obtaining 15 a pulse-phase difference map 17 identifying differences between the pulse-phase maps 11, 13 of the area 33;

obtaining 25 a shutter-time difference map 27 identifying differences between capture times of corresponding locations in the two images 5, 7; and correcting 29 the pulse-phase difference map 17 using the shutter-time difference map 27 to obtain a map 31 of pulse-phase changes which have occurred over a duration of a shutter scan.

In other examples, the apparatus 100 comprises: at least one processor 103; and at least one memory 105 including computer program code. The at least one memory 105 and the computer program code are configured to, with the at least one processor 103, cause the apparatus 100 at least to perform:

controlling 3 capture of two images 5, 7 of an area 33, across which a pulse propagates, using different shutter scanning directions 35, 43;

obtaining 19 a colour difference map 21 identifying differences between the two images 5, 7;

converting 23 the colour difference map 21 into a pulse-phase difference map 17;

obtaining 25 a shutter-time difference map 27 identifying differences between capture times of corresponding locations in the two images 5, 7; and correcting 29 the pulse-phase difference map 17 using the shutter-time difference map 27 to obtain a map 31 of pulse-phase changes which have occurred over a duration of a shutter scan.

As illustrated in FIG. 8, the computer program 107 may arrive at the apparatus 100 via any suitable delivery mechanism 109. The delivery mechanism 109 may be, for example, a machine readable medium, a computer-readable medium, a non-transitory computer-readable storage medium, a computer program product, a memory device, a record medium such as a Compact Disc Read-Only Memory (CD-ROM) or a Digital Versatile Disc (DVD) or a solid state memory, an article of manufacture that comprises or tangibly embodies the computer program 107. The delivery mechanism may be a signal configured to reliably transfer the computer program 107. The apparatus 100 may propagate or transmit the computer program 107 as a computer data signal.

Computer program instructions can perform at least the following or can cause an apparatus to perform at least the following:

causing control 3 of capture of two images 5, 7 of an area 33, across which a pulse propagates, using different shutter scanning directions 35, 43;

either: converting 9 the images 5, 7 into pulse-phase maps 11, 13 of the area 33 and obtaining 15 a pulse-phase difference map 17 identifying differences between the pulse-phase maps 11, 13 of the area 33; or obtaining 19 a colour difference map 21 identifying differences between the two images 5, 7 and converting 23 the colour difference map 21 into a pulse-phase difference map 17;

obtaining 25 a shutter-time difference map 27 identifying differences between capture times of corresponding locations in the two images 5, 7; and correcting 29 the pulse-phase difference map 17 using the shutter-time difference map 27 to obtain a map 31 of pulse-phase changes which have occurred over a duration of a shutter scan.

The computer program instructions may be comprised in a computer program 107, a non-transitory computer readable medium, a computer program product, a machine readable medium. In some but not necessarily all examples, the computer program instructions may be distributed over more than one computer program 107.

Although the memory 105 is illustrated as a single component/circuitry it may be implemented as one or more separate components/circuitry some or all of which may be integrated/removable and/or may provide permanent/semi-permanent/dynamic/cached storage.

Although the processor 103 is illustrated as a single component/circuitry it may be implemented as one or more separate components/circuitry some or all of which may be integrated/removable. The processor 103 may be a single core or multi-core processor.

References to 'computer-readable storage medium', 'computer program product', 'tangibly embodied computer program' etc. or a 'controller', 'computer', 'processor' etc. should be understood to encompass not only computers having different architectures such as single/multi-processor architectures and sequential (Von Neumann)/parallel architectures but also specialized circuits such as field-programmable gate arrays (FPGA), application specific circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term 'circuitry' may refer to one or more or all of the following:

(a) hardware-only circuitry implementations (such as implementations in only analog and/or digital circuitry) and (b) combinations of hardware circuits and software, such as (as applicable):

(i) a combination of analog and/or digital hardware circuit(s) with software/firmware and (ii) any portions of hardware processor(s) with software (including digital signal processor(s)), software, and memory(ies) that work together to cause an apparatus, such as a mobile phone or server, to perform various functions and (c) hardware circuit(s) and or processor(s), such as a microprocessor(s) or a portion of a microprocessor(s), that requires software (e.g. firmware) for operation, but the software may not be present when it is not needed for operation.

This definition of circuitry applies to all uses of this term in this application, including in any claims. As a further example, as used in this application, the term circuitry also covers an implementation of merely a hardware circuit or processor and its (or their) accompanying software and/or firmware. The term circuitry also covers, for example and if applicable to the particular claim element, a baseband integrated circuit for a mobile device or a similar integrated circuit in a server, a cellular network device, or other computing or network device.

The blocks illustrated in, or described with reference to, any preceding FIG may represent steps in a method and/or sections of code in the computer program 107. The illustration of a particular order to the blocks does not necessarily imply that there is a required or preferred order for the blocks and the order and arrangement of the block may be varied. Furthermore, it may be possible for some blocks to be omitted.

Where a structural feature has been described, it may be replaced by means for performing one or more of the functions of the structural feature whether that function or those functions are explicitly or implicitly described.

Consequently, in some examples, the apparatus 100 comprises means for:

controlling 3 capture of two images 5, 7 of an area 33, across which a pulse propagates, using different shutter scanning directions 35, 43;

converting 9 the images 5, 7 into pulse-phase maps 11, 13 of the area 33;

obtaining 15 a pulse-phase difference map 17 identifying differences between the pulse-phase maps 11, 13 of the area 33;

obtaining 25 a shutter-time difference map 27 identifying differences between capture times of corresponding locations in the two images 5, 7; and correcting 29 the pulse-phase difference map 17 using the shutter-time difference map 27 to obtain a map 31 of pulse-phase changes which have occurred over a duration of a shutter scan.

In other examples, the apparatus 100 comprises means for:

controlling 3 capture of two images 5, 7 of an area 33, across which a pulse propagates, using different shutter scanning directions 35, 43;

obtaining 19 a colour difference map 21 identifying differences between the two images 5, 7;

converting 23 the colour difference map 21 into a pulse-phase difference map 17; obtaining 25 a shutter-time difference map 27 identifying differences between capture times of corresponding locations in the two images 5, 7; and correcting 29 the pulse-phase difference map 17 using the shutter-time difference map 27 to obtain a map 31 of pulse-phase changes which have occurred over a duration of a shutter scan.

In some but not necessarily all examples, the apparatus 100 is configured to communicate data from the apparatus 100 with or without local storage of the data in a memory 105 at the apparatus 100 and with or without local processing of the data by circuitry or processors at the apparatus 100.

The data may, for example, be the map 31 of pulse-phase changes or the map 93 of colour change rates or data produced by the processing of the map 31 of pulse-phase changes or the map 93 of colour change rates such as, for example, information about the identity or health of a user's whose body surface was imaged in block 3 of method 1 or method 89.

The data may be stored in processed or unprocessed format remotely at one or more remote devices. The data may be stored in the Cloud.

The data may be processed remotely at one or more remote devices. The data may be partially processed locally and partially processed remotely at one or more remote devices.

The data may be communicated to the one or more remote devices wirelessly via short range radio communications such as Wi-Fi or Bluetooth, for example, or over long range cellular radio links. The apparatus 100 may comprise a communications interface such as, for example, a radio transceiver for communication of data.

The apparatus 100 may be part of the Internet of Things forming part of a larger, distributed network.

The processing of the data, whether local or remote, may be for the purpose of identification, authorisation, health monitoring, data aggregation, patient monitoring, vital signs monitoring or other purposes.

The processing of the data, whether local or remote, may produce an output. The output may be communicated to the apparatus 100 which may cause the device 79 to produce an output sensible to the subject such as an audio output, visual output or haptic output.

The use of the term 'capture' in relation to an image relates to temporary recording of the data of the image. Temporary recording implies the recording of data temporarily. This may, for example, occur during sensing or image capture, occur at a dynamic memory, occur at a buffer such as a circular buffer, a register, a cache or similar. Captured images may be stored by permanent recording of the data of the image. Permanent recording implies that the data is in the form of an addressable data structure that is retrievable from an addressable memory space and can therefore be stored and retrieved until deleted or over-written, although long-term storage may or may not occur.

The above-described examples find application as enabling components of: automotive systems; telecommunication systems; electronic systems including consumer electronic products; distributed computing systems; media systems for generating or rendering media content including audio, visual and audio visual content and mixed, mediated, virtual and/or augmented reality; personal systems including personal health systems or personal fitness systems; navigation systems; user interfaces also known as human machine interfaces; networks including cellular, non-cellular, and optical networks; ad-hoc networks; the internet; the internet of things; virtualized networks; and related software and services.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one" or by using "consisting".

In this description, reference has been made to various examples. The description of features or functions in relation to an example indicates that those features or functions are present in that example. The use of the term 'example' or 'for example' or 'can' or 'may' in the text denotes, whether explicitly stated or not, that such features or functions are present in at least the described example, whether described as an example or not, and that they can be, but are not necessarily, present in some of or all other examples. Thus 'example', 'for example', 'can' or 'may' refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example as part of a working combination but does not necessarily have to be used in that other example.

Although examples have been described in the preceding paragraphs with reference to various examples, it should be appreciated that modifications to the examples given can be made without departing from the scope of the claims.

Features described in the preceding description may be used in combinations other than the combinations explicitly described above.

Although functions have been described with reference to certain features, those functions may be performable by other features whether described or not.

Although features have been described with reference to certain examples, those features may also be present in other examples whether described or not.

The term 'a' or 'the' is used in this document with an inclusive not an exclusive meaning. That is any reference to X comprising a/the Y indicates that X may comprise only one Y or may comprise more than one Y unless the context clearly indicates the contrary. If it is intended to use 'a' or 'the' with an exclusive meaning then it will be made clear in the context. In some circumstances the use of 'at least one' or 'one or more' may be used to emphasis an inclusive meaning but the absence of these terms should not be taken to infer any exclusive meaning.

The presence of a feature (or combination of features) in a claim is a reference to that feature or (combination of features) itself and also to features that achieve substantially the same technical effect (equivalent features). The equivalent features include, for example, features that are variants and achieve substantially the same result in substantially the same way. The equivalent features include, for example, features that perform substantially the same function, in substantially the same way to achieve substantially the same result.

In this description, reference has been made to various examples using adjectives or adjectival phrases to describe characteristics of the examples. Such a description of a characteristic in relation to an example indicates that the characteristic is present in some examples exactly as described and is present in other examples substantially as described.

Whilst endeavouring in the foregoing specification to draw attention to those features believed to be of importance it should be understood that the Applicant may seek protection via the claims in respect of any patentable feature or combination of features hereinbefore referred to and/or shown in the drawings whether or not emphasis has been placed thereon.

We claim:

1. An apparatus comprising:
   at least one processor; and
   at least one memory including computer program code,
   the at least one memory and the computer program code configured to, when executed by the at least one processor, cause the apparatus at least to:
   control capture of two images of an area, across which a pulse propagates, using different shutter scanning directions;
   convert the images into pulse-phase maps of the area;
   obtain a pulse-phase difference map identifying differences between the pulse-phase maps of the area;
   obtain a shutter-time difference map identifying differences between capture times of corresponding locations in the two images; and
   correct the pulse-phase difference map using the shutter-time difference map to obtain a map of pulse-phase changes which have occurred over a duration of a shutter scan.

2. An apparatus according to claim 1 wherein the control of the capture of the two images comprises at least one of:
   control timing of capture based on a pulse interval; or
   control timing of capture to follow capture of respective reference images of the area using the same shutter scanning direction after a delay of the same duration.

3. An apparatus according to claim 1 wherein the control of the capture of the two images further comprises; control timing of capture to coincide with propagation of a feature of a pulse waveform through a portion of the area.

4. An apparatus according to claim 1 wherein the control of the capture of the two images further comprises; configure settings of one or more of:
   an angle between the different shutter scanning directions;
   a shutter scanning speed; or
   a shutter aperture size,
   to achieve differences in capture times between a first subset of corresponding locations in the two images which are of greater duration than differences in capture times between a second subset of corresponding locations in the two images, wherein the first subset represents a portion of the area and the second subset represents another portion of the area.

5. An apparatus according to claim 1 wherein, based on a target difference in capture times between corresponding locations in the two images or a target duration of a shutter scan, said control of the capture of the two images further comprises; configure settings of one or more of:
   an angle between the different shutter scanning directions;
   a shutter scanning speed; or
   a shutter aperture size.

6. An apparatus according to claim 1 wherein the obtaining of the pulse-phase difference map from the two images further comprises; use of a stored periodic relationship between color of the area and time to infer a pulse-phase from a color.

7. An apparatus according to claim 1 wherein the correcting of the pulse-phase difference map further comprises:
   based on a pulse interval, convert the shutter-time difference map to a shutter-phase difference map; and
   subtract the shutter-phase difference map from the pulse-phase difference map.

8. An apparatus according to claim 1 wherein the computer program code with the at least one processor are further configured to cause one or more rotary actuators to rotate an image sensor to enable capture of the area using the different shutter scanning directions.

9. An apparatus according to claim 1 wherein the computer program code with the at least one processor are further configured to cause the apparatus to: provide guidance to a user between capture of the two images, the guidance indicating a manual rotation of an image sensor or the area for enabling capture of the area using the different shutter scanning directions.

10. An apparatus according to claim 1 wherein the computer program code with the at least one processor are further configured to cause the apparatus to: trigger capture of a second of the two images in response to a determination of an orientation change between the area and an image sensor for enabling capture of the area using the different shutter scanning directions.

11. An apparatus according to claim 1 wherein the control of the capture of the two images further comprises; trigger, at the same time, capture using two image sensors having different shutter scanning directions.

12. An apparatus according to claim 1 wherein the control of the capture of the two images is triggered by an authentication request event.

13. An apparatus comprising:

at least one processor; and at least one memory including computer program code, the at least one memory and the computer program code configured to, when executed by the at least one processor, cause the apparatus at least to:

control capture of two images of an area, across which a pulse propagates, using different shutter scanning directions;

obtain a color difference map identifying differences between the two images;

convert the color difference map into a pulse-phase difference map;

obtain a shutter-time difference map identifying differences between capture times of corresponding locations in the two images; and correct the pulse-phase difference map using the shutter-time difference map to obtain a map of pulse-phase changes which have occurred over a duration of a shutter scan.

14. A method comprising:

controlling capture of two images of an area, across which a pulse propagates, using different shutter scanning directions;

converting the images into pulse-phase maps of the area and obtaining a pulse-phase difference map identifying differences between the pulse-phase maps of the area;

obtaining a shutter-time difference map identifying differences between capture times of corresponding locations in the two images; and correcting the pulse-phase difference map using the shutter-time difference map to obtain a map of pulse-phase changes which have occurred over a duration of a shutter scan.

15. A method according to claim 14 wherein controlling the capture of the two images comprises at least one of:

controlling timing of capture based on a pulse interval; or controlling timing of capture to follow capture of respective reference images of the area using the same shutter scanning direction after a delay of the same duration.

16. A method according to claim 14 wherein controlling the capture of the two images comprises controlling timing of capture to coincide with propagation of a feature of a pulse waveform through a portion of the area.

17. A method according to claim 14 wherein, based on a target difference in capture times between corresponding locations in the two images or a target duration of a shutter scan, said controlling the capture of the two images comprises configuring settings of one or more of:

an angle between the different shutter scanning directions;

a shutter scanning speed; or a shutter aperture size.

18. A non-transitory computer readable medium comprising program instructions stored thereon for causing an apparatus to perform at least the following:

controlling capture of two images of an area, across which a pulse propagates, using different shutter scanning directions;

obtaining a color difference map identifying differences between the two images and converting the color difference map into a pulse-phase difference map;

obtaining a shutter-time difference map identifying differences between capture times of corresponding locations in the two images; and correcting the pulse-phase difference map using the shutter-time difference map to obtain a map of pulse-phase changes which have occurred over a duration of a shutter scan.

19. The non-transitory computer readable medium of claim 18, wherein controlling the capture of the two images comprises at least one of:

controlling timing of capture based on a pulse interval; or controlling timing of capture to follow capture of respective reference images of the area using the same shutter scanning direction after a delay of the same duration.

20. The non-transitory computer readable medium of claim 18, wherein controlling the capture of the two images comprises controlling timing of capture to coincide with propagation of a feature of a pulse waveform through a portion of the area.

* * * * *